(12) United States Patent
Guo et al.

(10) Patent No.: US 11,134,961 B2
(45) Date of Patent: Oct. 5, 2021

(54) MAGNETIC DRIVE MEDICAL HANDPIECE

(71) Applicant: CHONGQING XISHAN SCIENCE & TECHNOLOGY CO., LTD., Chongqing (CN)

(72) Inventors: Yijun Guo, Chongqing (CN); Xinyun Zhang, Chongqing (CN); Qunying Wang, Chongqing (CN); Jinbin Zhang, Chongqing (CN)

(*) Notice: Subject to any disclaimer, the term of this patent is extended or adjusted under 35 U.S.C. 154(b) by 350 days.

(21) Appl. No.: 16/304,713

(22) PCT Filed: May 11, 2017

(86) PCT No.: PCT/CN2017/083891
§ 371 (c)(1),
(2) Date: Nov. 28, 2018

(87) PCT Pub. No.: WO2017/206691
PCT Pub. Date: Dec. 7, 2017

(65) Prior Publication Data
US 2020/0323542 A1    Oct. 15, 2020

(30) Foreign Application Priority Data

May 31, 2016 (CN) .......................... 201610374434.7
Apr. 27, 2017 (CN) .......................... 201720458885.9

(51) Int. Cl.
*A61B 17/16* (2006.01)
*A61B 17/32* (2006.01)
*A61B 17/00* (2006.01)

(52) U.S. Cl.
CPC ...... *A61B 17/1624* (2013.01); *A61B 17/1631* (2013.01); *A61B 17/1633* (2013.01); *A61B 17/32* (2013.01); *A61B 2017/00876* (2013.01); *A61B 2017/320004* (2013.01); *A61B 2217/007* (2013.01)

(58) Field of Classification Search
CPC ............ A61B 17/1624; A61B 17/1631; A61B 17/1633; A61B 17/32; A61B 2017/00876; A61B 2017/320004; A61B 2017/007
See application file for complete search history.

(56) References Cited

U.S. PATENT DOCUMENTS

2010/0217245 A1    8/2010   Prescott
2016/0074057 A1    3/2016   Jezierski

FOREIGN PATENT DOCUMENTS

| CN | 101568309 A | 10/2009 |
| CN | 103298423 A | 9/2013 |
| CN | 105943115 A | 9/2016 |
| CN | 205866801 U | 1/2017 |
| EP | I362559 A1 | 11/2003 |

*Primary Examiner* — Kathleen S Holwerda
*Assistant Examiner* — Brooke Labranche
(74) *Attorney, Agent, or Firm* — Global IP Services; Tianhua Gu

(57) ABSTRACT

A magnetic drive medical handpiece includes a handpiece housing (1), and a magnetic power output assembly (20) and a magnetic power input assembly (30), where the magnetic power output assembly (20) is configured to be in connected transmission with a cutting tool, the magnetic power input assembly (30) is in transmission fit with a power apparatus and is configured to drive, by using magnetic force, the magnetic power output assembly (20) to rotate, and a separation member (2) configured to form an axial static seal is disposed between the magnetic power output assembly (20) and the magnetic power input assembly (30).

18 Claims, 5 Drawing Sheets

MAGNETIC DRIVE MEDICAL HANDPIECE

CROSS REFERENCE TO RELATED PATENT APPLICATION

The present application is the US national stage of PCT/CN2017/083891 filed on May 11, 2017, which claims the priorities of the Chinese patent applications No. 201610374434.7 filed on May 31, 2016 and No. 201720458885.9 filed on Apr. 27, 2017, which applications are incorporated herein by reference.

FIELD OF DISCLOSURE

The present disclosure relates to the field of medical appliances, and in particular, to a magnetic drive medical handpiece.

DESCRIPTION OF RELATED ARTS

In surgeries of bone tissue or soft tissue grinding and resection, a handpiece and a cutting tool that rotates at a high speed and that is mounted on the handpiece are usually used for processing such as abrasive drilling and planing. A micromotor is usually mounted in the handpiece and transmits power to the cutting tool by using a transmission member. To clean up, in time, blood and physiological saline that obstruct the visual field during the surgery, a suction channel for sucking blood and physiological saline is usually disposed on the handpiece. When necessary, a water injection channel for perfusion of physiological saline may also be provided. The suction channel is in communication with an inner chamber of a front end of the handpiece and the suction flow is controlled by using a regulating valve. In order to prevent the blood and physiological saline from wetting a decelerator and the micromotor in the handpiece, a seal member is usually disposed on an outer circle of the transmission member to form an axial dynamic seal, so as to prevent liquid in the inner chamber of the front end of the handpiece from flowing into an inner chamber of a rear end of the handpiece. However, because the seal member is usually a rubber ring seal or a ceramic seal and is a dynamic seal, when the transmission member rotates, relative rotation exists between the transmission member and the seal member and/or between a housing of the handpiece and the seal member, which results in micro leakage. Consequently, the service life of the motor is short. In addition, the seal member is usually in contact with the blood and the physiological saline, and after heat sterilization, sodium chloride crystals are easily formed on a seal surface of the handpiece, and a seal failure is usually caused after rotation. Consequently, the decelerator and the motor bearing are corroded by rust and get stuck, which leads to high maintenance and repair costs, and the stability of clinical use is affected.

SUMMARY OF THE PRESENT DISCLOSURE

In view of this, the objective of the present disclosure is to overcome defects in the prior art, and provide a magnetic drive medical handpiece. Power is transmitted by means of magnetic coupling, and a cutting tool is stably driven to rotate, so that high transmission efficiency is achieved. In addition, an effective axial seal is formed in an inner chamber of a handpiece, to avoid leakage, and prevent a decelerator and a micromotor in the handpiece from being corroded, thereby greatly improving the service life, and clinical use stability of the handpiece.

The magnetic drive medical handpiece consistent with the present disclosure comprises a handpiece housing, and a magnetic power output assembly and a magnetic power input assembly wherein the magnetic power output assembly and the magnetic power input assembly are disposed in parallel along an axial direction in the handpiece housing, the magnetic power output assembly is configured to be in connected transmission with a cutting tool, the magnetic power input assembly is in transmission fit with a power apparatus and is configured to drive, by using magnetic force, the magnetic power output assembly to rotate, and a separation member configured to form an axial static seal is disposed between the magnetic power output assembly and the magnetic power input assembly.

The present disclosure has the following beneficial effects: power of a power apparatus is input by using a magnetic power input assembly, the magnetic power input assembly drives, by using magnetic force, a magnetic power output assembly to rotate, thereby driving a cutting tool to rotate, and a separation member that forms a static seal is disposed between the magnetic power input assembly and the magnetic power output assembly. In this way, micro leakage of a handpiece housing caused by pool sealing of a dynamic seal is avoided, and a decelerator and a micromotor in a handpiece are prevented from being corroded, and the service life, and clinical use safety and stability of the handpiece are greatly improved. Power is transmitted by means of magnetic coupling, so that the cutting tool is stably driven to rotate and high transmission efficiency is achieved. After the cutting tool is mounted on the handpiece, axial and radial anti-loading capabilities are strong, and an anti-bending-moment capability is also relatively strong, to avoid unstable power transmission or large loss, thereby ensuring the high efficiency of a surgery.

BRIEF DESCRIPTION OF THE DRAWINGS

The present disclosure is further described below with reference to the accompanying drawings and embodiments.

DETAILED DESCRIPTION OF THE PREFERRED EMBODIMENTS

Figure 1:
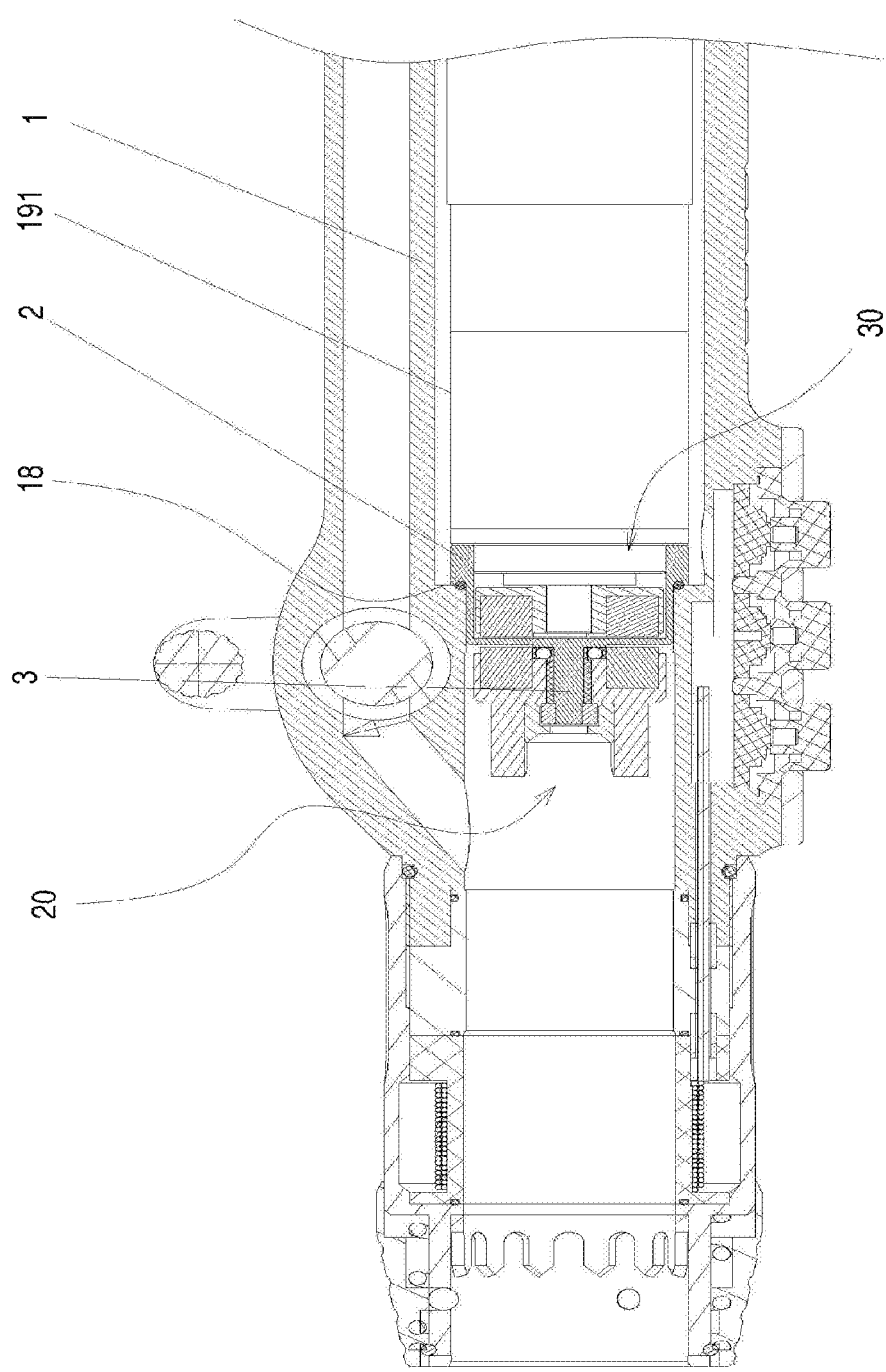
FIG. 1 is a schematic structural diagram of a magnetic drive medical handpiece of the present disclosure.

As shown in FIG. 1, a magnetic drive medical handpiece in this embodiment comprises a handpiece housing 1, and a magnetic power output assembly 20 and a magnetic power input assembly 30, the magnetic power output assembly 20 and the magnetic power input assembly 30 are disposed in the handpiece housing 1 in parallel along an axial direction. The magnetic power output assembly 20 is configured to be in connected transmission with a cutting tool (not shown). The magnetic power input assembly 30 is in transmission fit with a power apparatus (not shown). When the power apparatus outputs power to drive the magnetic power input assembly 30 to rotate, the magnetic power output assembly 20 is driven to rotate, by using magnetic force generated between the magnetic power input assembly 30 and the magnetic power output assembly 20. A separation member 2 configured to form an axial static seal is disposed between the magnetic power output assembly 20 and the magnetic power input assembly 30. Transmission fit between the magnetic power output assembly 20 and the cutting tool, and transmission fit between the magnetic power input assembly 30 and the power apparatus may be implemented by using any transmission structure that can implement the present disclosure in the prior art, and details are not described herein. The separation member 2 may be an occluder made of a nonmagnetic material, and a seal ring may be disposed on an outer circle of the occluder to form the axial static seal, and the axial static seal indicates that the separation member 2 divides the handpiece housing 1 into two chambers in a sealing manner along an axial direction. Power is transmitted by means of magnetic coupling, so that the cutting tool is stably driven to rotate. The separation member 2 does not rotate along with driving of the power input or output assembly, so as to avoid micro leakage of conventional dynamic seal caused by poor sealing due to rotation of the power input or output assembly, thereby preventing a decelerator and a micromotor in a handpiece from being corroded, greatly improving the service life, and clinical use safety and stability of the handpiece, and achieving a high transmission efficiency.

In this embodiment, the magnetic power input assembly 30 drives, by using axial magnetic force, the magnetic power output assembly 20 to rotate. The separation member 2 is detachably fixedly connected to the handpiece housing 1, and a front end face of the separation member 2 axially protrudes forward to form a support shaft 3. The magnetic power output assembly 20 rotates and is sleeved over the support shaft 3 in an axial limiting manner. An end on which the cutting tool is mounted along the axial direction of the handpiece housing 1 is a front end, and an opposite end is a rear end. The support shaft 3 is disposed to ensure the coaxiality of the magnetic power output assembly 20 and the magnetic power input assembly 30, so that to achieve highly efficient power transmission. Because the magnetic power input assembly 30 drives, by using the axial magnetic force, the magnetic power output assembly 20 to rotate, the support shaft 3 can be used to ensure that force applied to the magnetic power output assembly 20 is stable, thereby preventing the magnetic power output assembly 20 from shaking.

Figure 2:
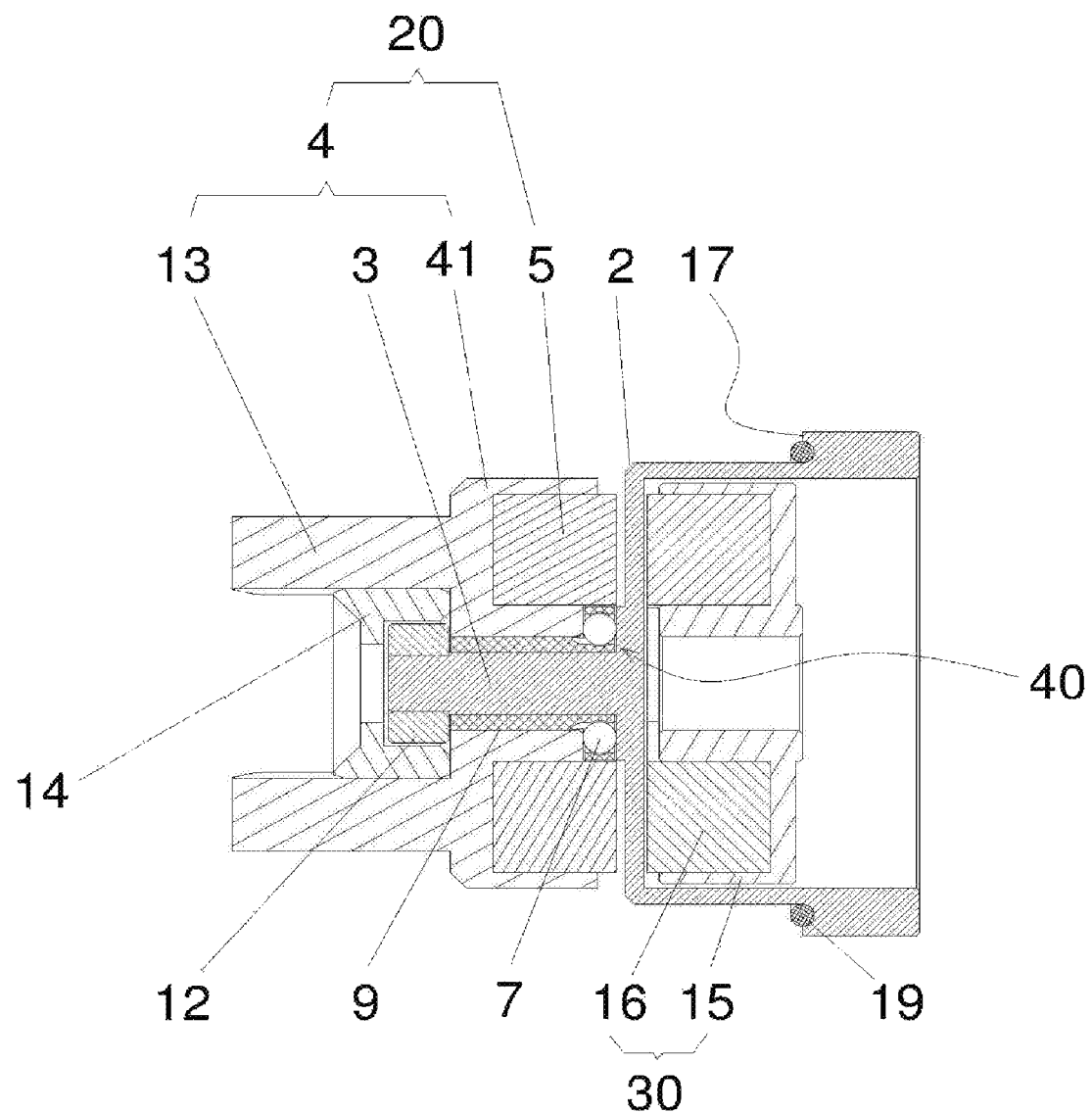
FIG. 2 is a schematic structural diagram of an axial seal in an embodiment of the present disclosure.

In an embodiment of an axial seal in the present disclosure, as shown in FIG. 2, the magnetic power output assembly 20 comprises a power output member 4 in connected transmission fit with the cutting tool and a driven magnet 5 fixed to the power output member 4, the power output member 4 is sleeved over the support shaft 3 and an axial rear end face of the power output member 4 is in rotation fit with an axial front end face of the separation member 2 by using a plane bearing 40. The power output member 4 may be a ring or a disk sleeved over the support shaft 3. The power output member 4 is provided with a combination portion in connected transmission with the cutting tool, for example, a circumferential tooth or a circumferential groove. The plane bearing 40 is disposed to ensure that the power output member 4 can bear large axial load, thereby ensuring the stability of transmission. In addition, because a shifting of the power output member 4 only has an axial direction, which is the same as a coupling magnetic direction, the driving magnet 16 does not move along a direction perpendicular to the magnetic direction relative to the driven magnet 5, which effectively avoids additional moment caused by relative movement of the driving magnet 16 and the driven magnet 5 along the direction perpendicular to the magnetic direction, additional moment has an adverse effect on the axial seal. Even if the power output member 4 slightly moves along the axial direction, moment transmission between the magnetic power input assembly 30 and the magnetic power output assembly 20 by using the axial magnetic force will not be affected. In particular, after long-time use, when the plane bearing 40 applies pressure to the front end face of the separation member 2 to form an annular pressure groove, the annular pressure groove radially limits the plane bearing 40, to ensure stable and highly efficient power moment transmission.

Figure 3:
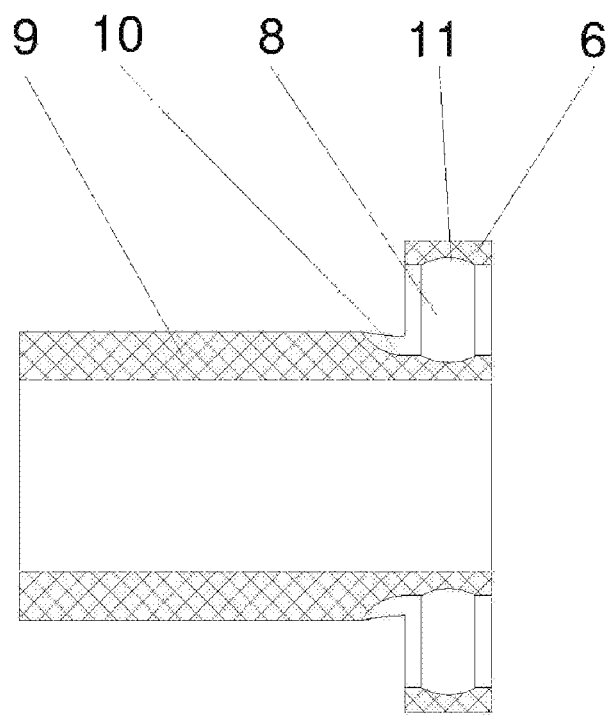
FIG. 3 is a schematic structural diagram of an annular retainer and a support sleeve in the present disclosure.

In this embodiment, as shown in FIG. 3, the plane bearing 40 comprises an annular retainer 6 and a plurality of balls 7 distributed on the annular retainer 6 along a circumferential direction. The annular retainer 6 is sleeved over the support shaft 3 and is provided, along an axial direction, with mounting holes 8 for mounting the balls 7, and the diameter of the ball 7 is greater than the axial length of the mounting hole 8. In this embodiment, there is a plurality of balls 7, which may be steel balls. The diameter of the ball 7 is greater than the axial length of the mounting hole 8, so that it is ensured that the rear end face of the power output member 4 is in rolling friction with the front end face of the separation member 2, which greatly reduces heat generated by friction. In particular, when axial load of the power output member 4 is large, friction is reduced to reduce a power loss, thereby improving a power output efficiency.

In this embodiment, an inner circle of the annular retainer 6 extends forward along an axial direction to form a support sleeve 9, and the support sleeve 9 is radially supported between the power output member 4 and the support shaft 3 in a manner of sliding along a circumferential direction. The support sleeve 9 is disposed as a specially-made sliding bearing of the power output member 4, and is engaged with the plane bearing 40 to form a compounded centrifugal thrust bearing, so that the magnetic drive medical handpiece can bear large load along the axial direction and the radial direction, and the friction is small, the power transmission efficiency is high, and transmission is stable, so that clamping-to-stopping is avoided, and the structure is simple and compact.

In this embodiment, the mounting hole 8 is disposed at a joint between the annular retainer 6 and the support sleeve 9, the diameter of a rear end opening of the mounting hole 8 is less than the diameter of the ball 7, a rear end outer circle of the support sleeve 9 is recessed inward along a radial direction to form a semi-arc-shaped groove 10 in communication with a front end opening of the mounting hole 8, the ball 7 is embedded into the mounting hole 8 by means of engagement between the front end opening and the semi-arc-shaped groove 10, to facilitate mounting of the ball 7; an arc-shaped annular groove 11 is disposed in the middle of an inner circle of the mounting hole 8, and the radian of the arc-shaped annular groove 11 matches the radian of an outer surface of the ball 7, so as to effectively prevent the ball 7 from falling off the mounting hole 8 during mounting, thereby improving the mounting efficiency.

In this embodiment, a front end of the support shaft 3 is provided with a limiting ring 12 in a fixed sleeving manner, and an axial rear end face of the limiting ring 12 is used for positioning the power output member 4 along an axial direction; the power output member 4 comprises a power output ring 41 and a driving shift fork 13 formed by means of axial protrusion of a front end face of the power output ring 41, there is a plurality of driving shift forks 13 distributed along a circumferential direction. The magnetic drive medical handpiece further comprises a positioning sleeve 14 for axially positioning the cutting tool, the positioning sleeve 14 is fixedly disposed, in a manner in which an axial rear end face of the positioning sleeve 14 abuts against the power output ring 41, in an inner circle formed by the plurality of driving shift forks 13. A shift fork groove engaged with the driving shift fork 13 is formed by using a rear end of the cutting tool. The driving shift fork 13 is inserted into the shift fork groove for circumferential transmission, and the mounting is convenient and the structure is stable. In addition, when the cutting tool is mounted, axial positioning is performed by using the positioning sleeve 14, and axial load of the cutting tool is transmitted to the power output ring 41 by using the positioning sleeve 14, to ensure that load force is axially transmitted and uniformly distributed along the circumferential direction, thereby avoiding an additional moment generated by transmitting the axial load by the driving shift fork 13.

In this embodiment, a decelerator 191 is further disposed between the magnetic power input assembly 30 and the power apparatus, the magnetic power input assembly 30 comprises a power input member 15 sleeved over an output shaft of the decelerator 191 in a circumferential transmission manner and a driving magnet 16 fixed to the power input member 15. The driving magnet 16 and the driven magnet 5 face to each other and attract each other along an axial direction, and an axial gap is disposed between the driving magnet 16 and the separation member 2 and an axial gap is disposed between the driven magnet 5 and the separation member 2. As shown in the figures, there is a plurality of driving magnets 16 and a plurality of driven magnets 5, and the number of the driving magnets 16 is the same as that of the driven magnets 5. The driving magnets 16 and the driven magnets 5 are respectively embedded into axial end faces of the corresponding power output member 4 (the rear end face) and the power input member 15 (the front end face) and are fixed, and the axial gap is suitably set to ensure that the maximum anti-torque between the driving magnet 16 and the driven magnet 5 is large, so as to avoid slippage.

Figure 4:
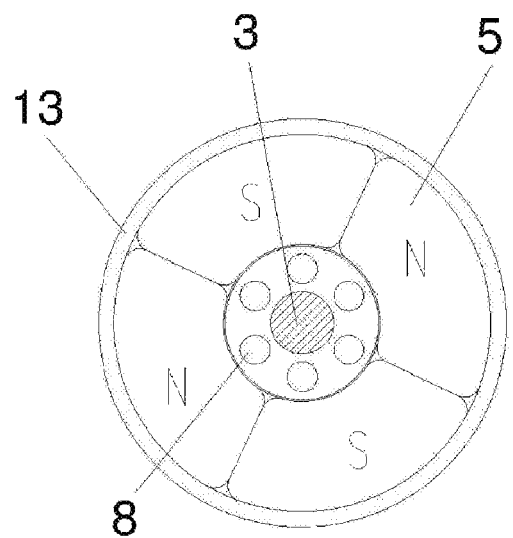
FIG. 4 is a schematic structural diagram of a rear end face of a power output member in the present disclosure.
Figure 5:
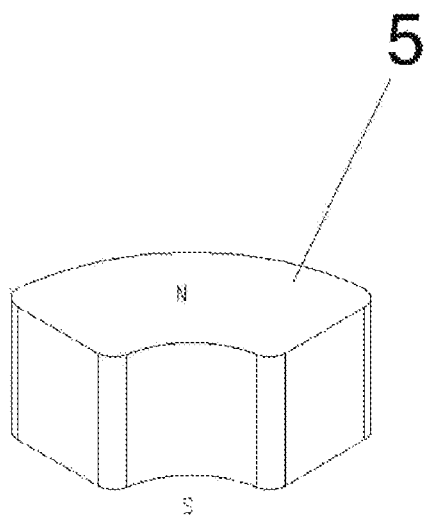
FIG. 5 is a schematic structural diagram of an arc-shaped magnetic tile in the present disclosure.

In this embodiment, as shown in FIG. 4 and FIG. 5, the driving magnet 16 and the driven magnet 5 are both arc-shaped magnetic tiles. A plurality of arc-shaped magnetic tiles are uniformly distributed along a circumferential direction, and same axial ends of two arc-shaped magnetic tiles that are adjacent in the circumferential direction are heteropoles. In this way, it is ensured that the driving magnet 16 and the driven magnet 5 can quickly recover magnetic coupling transmission when slipping in the circumferential direction due to bearing an overload torque.

In this embodiment, the separation member 2 is a separation sleeve having a closed front end, an outer circle of the separation sleeve forms an annular step I 17 and is in lap fit with an annular step II 18 to implement axial limitation of the separation sleeve, the annular step II 18 is disposed in an inner circle of the handpiece housing 1, an O-shaped seal ring 19 is disposed on an axial opposite surface of the annular step I 17 and the annular step II 18. As shown in the figures, a front section of the outer circle of the separation sleeve is recessed inward and forms the annular step I 17 with a rear section, an inner circle of the handpiece housing 1 protrudes inward corresponding to the front section of the outer circle of the separation sleeve, and is engaged with the front section of the outer circle of the separation sleeve in a conformal manner and performs radial limitation, to ensure the stability of the separation member 2. In addition, the O-shaped seal ring 19 is disposed on the axial opposite surface of the annular step I 17 and the annular step II 18. After mounting, the rear end of the separation sleeve is provided with an axially forward preload, to ensure that the O-shaped seal ring 19 receives axial compacting force, and achieve a good sealing effect. Certainly, the axially forward preload may be applied by a circular nut threadedly sleeved in the handpiece housing 1, this belongs to the prior art, and is not described in detail herein.

Figure 6:
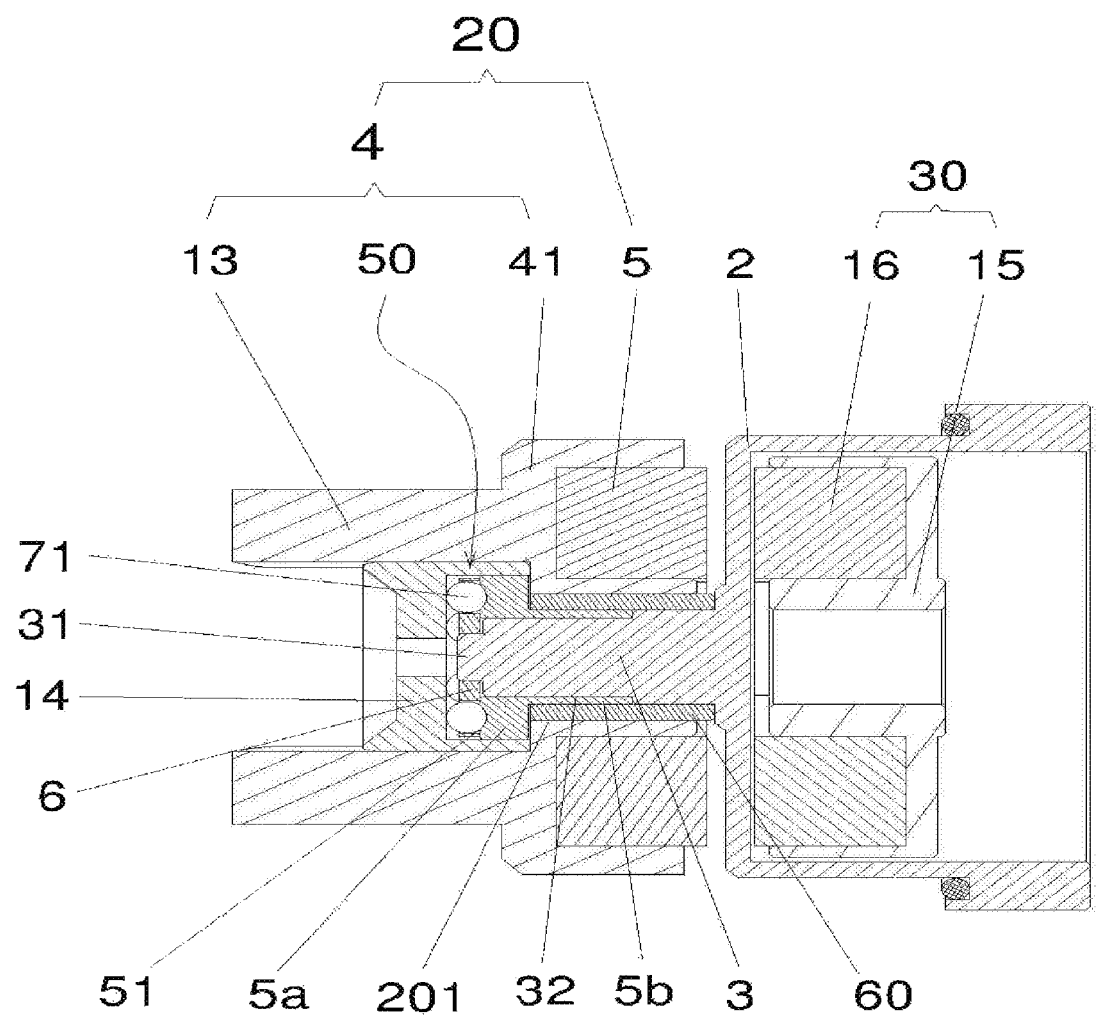
FIG. 6 is a schematic structural diagram of an axial seal in another embodiment of the present disclosure.

In another embodiment of an axial seal in the present disclosure, as shown in FIG. 6, different from the embodiment shown in FIG. 2, in the embodiment of FIG. 6, the plane bearing 40 is not disposed on the axial rear end face of the power output member 4, a plane bearing 50 is provided in the magnetic drive medical handpiece the plane bearing 50 can limit the magnetic power output assembly 20 backward along the axial direction, the magnetic power output assembly 20 is provided with a shaft hole 201 corresponding to the support shaft 3, and the plane bearing 50 is located on a front end of the shaft hole 201.

Specifically, the hollow shaft hole 201 is formed at a position where the magnetic power output assembly 20 rotates and is sleeved over the support shaft 3; after the support shaft 3 is inserted into the shaft hole 201, the magnetic power output assembly 20 is in rotation fit with the support shaft 3; the shaft hole 201 is formed along an axial direction in the middle of the power output member 4 of the magnetic power output assembly 20 in this embodiment; the plane bearing 50 is located on a front end of the shaft hole 201 and is located, along the axial direction, on the front end (when the support shaft is short) or in the middle (when the support shaft is long) of the support shaft 3; the plane bearing 50 is disposed on the front end, corresponding to the shaft hole 201, of the support shaft 3 to form axial rolling support for the magnetic power output assembly 20, to ensure that the magnetic power output assembly 20 rotates smoothly and stably, so that the diameter of a rear axial section of the support shaft 3 can be set to be large, to ensure a high strength of the support shaft 3, and avoid breaking of the support shaft 3 in a use process, thereby further improving the service life of the handpiece; the plane bearing 50 may be prior art, and is not described in detail herein.

In this embodiment, a front end outer circle of the support shaft 3 is fixedly provided with a fixed ring 5a, a front end face of the fixed ring 5a supports the plane bearing 50 forward, and a rear end face of the fixed ring 5a is used for limiting the magnetic power output assembly 20 forward along an axial direction; the magnetic power input assembly 30 located on the rear end attracts the magnetic power output assembly 20 backward by using magnetic force, so that the plane bearing 50 is supported on the magnetic power output assembly 20 forward, thereby facilitating stable rotation of the magnetic power output assembly 20 in a case of balanced axial force; the plane bearing 50 effectively reduces rotation resistance of the magnetic power output assembly 20; the fixed ring 5a may be sleeved over the front end outer circle of the support shaft 3 in an interference fit manner, and the rear end face of the fixed ring 5a acts on the front end face of the power output member 4 in the magnetic power output assembly 20, thereby forming forward limitation on the magnetic power output assembly 20 along the axial direction, and preventing the magnetic power output assembly 20 from falling off. The structure is simple and compact, and is convenient to assemble.

In this embodiment, the plane bearing 50 comprises an annular retainer 6 and a plurality of rollers 71 distributed on the annular retainer 6 along a circumferential direction, and a front end face of the fixed ring 5a is provided with an annular groove 51 configured to guide the roller 71 along a circumferential direction. In a specific embodiment, the roller 71 may be a roller pin, a columnar roller, or a ball; a cross section of the annular groove 51 corresponding to the roller pin or the columnar roller is a rectangle (note: the difference between the roller pin and the columnar roller is that the aspect ratios are different); a cross section of the annular groove 51 corresponding to the ball is arc-shaped, and a partial outer wall of the ball is embedded into the annular groove 51 in a conformal manner. In the present disclosure, the roller 71 is guided by using the annular groove 51, to ensure a high stability of rotation of the plane bearing 50 and facilitate high coaxiality of a central shaft around which the magnetic power output assembly 20 rotates and the support shaft 3, thereby ensuring stable rotation of the magnetic power output assembly 20.

In this embodiment, the middle of a front end face of the support shaft 3 protrudes forward along an axial direction to form a mounting column 31, and the plane bearing 50 is rotatably sleeved over an outer circle of the mounting column 31. The mounting column 31 forms radial limitation to the annular retainer 6, to ensure stable rotation of the annular retainer 6.

In this embodiment, a rear end face of the fixed ring 5a extends backward along an axial direction to form a connection sleeve 5b sleeved over the support shaft 3, the fixed ring 5a and the connection sleeve 5b form a T-shaped sleeve together, and an inner circle of the T-shaped sleeve is fixedly connected to an outer circle of the support shaft 3. The connection sleeve 5b is sleeved in the shaft hole 201 in a conformal manner; the inner circle of the T-shaped sleeve may be fixed to the outer circle of the support shaft 3 in an interference fit manner, and assembly is firm and convenient; in addition, the T-shaped sleeve is sleeved over the support shaft 3, so that vertical precision of the front end face of the fixed ring 5a and the central axis of the support shaft 3 is improved, thereby ensuring stable support of the plane bearing 50 and the fixed ring 5a, as well as improving the fixing strength between the fixed ring 5a and the support shaft 3.

In this embodiment, the front end outer circle of the support shaft 3 is recessed to form a sinking platform 32, the inner circle of the T-shaped sleeve is fixedly sleeved over a platform surface of the sinking platform 32. The sinking platform 32 has a height the same as the thickness of the connection sleeve 5b. In this way, the outer circle of the connection sleeve 5b is leveled with the rear end outer circle of the support shaft 3, so as to effectively support the magnetic power output assembly 20 along a radial direction, thereby ensuring stable rotation of the magnetic power output assembly 20. Certainly, the connection sleeve 5b may also be integrally disposed in the inner circle of the annular driving claw 131 or runs through the shaft hole 201. In this embodiment, the height of the sinking platform 32 is designed to be equal to the thickness of the connection sleeve 5b, and the rear end of the support shaft 3 and the connection sleeve 5b are both disposed in the shaft hole 201, to ensure a stable and compact structure of the T-shaped sleeve, and also facilitate a large diameter of the rear end of the support shaft 3.

In this embodiment, a rotation sliding sleeve 60 is disposed in the shaft hole 201, and the rotation sliding sleeve 60 is in rotation fit with the shaft hole 201. As shown in the figures, the rotation sliding sleeve 60 may rotate relative to an inner wall of the shaft hole 201, and the rotation sliding sleeve 60 may also rotate with respect to the outer circle of the connection sleeve 5b and the rear end outer circle of support shaft 3 simultaneously; the rotation sliding sleeve 60 is made of a self-lubricant material; the rotation sliding sleeve 60 is used to reduce rotation friction force of the magnetic power output assembly 20, thereby ensuring high-speed rotation of the magnetic power output assembly 20.

Finally, it should be noted that the foregoing embodiments are only used to describe and not to limit the technical solutions of the present disclosure. Although the present disclosure has been described in detail with reference to preferred embodiments, a person of ordinary skill in the art should understand that the technical solutions of the present disclosure may be modified or equivalently replaced without departing from the spirit and scope of the technical solutions of the present disclosure. These modifications or equivalent replacements shall all fall within the scope of the claims of the present disclosure.

What is claimed is:

1. A magnetic drive medical handpiece, comprising a handpiece housing, a magnetic power output assembly, and a magnetic power input assembly, wherein the magnetic power output assembly and the magnetic power input assembly are disposed in parallel along an axial direction in the handpiece housing, the magnetic power output assembly is configured to be in connected transmission with a cutting tool, the magnetic power input assembly is in transmission fit with a power apparatus and is configured to drive, by using magnetic force, the magnetic power output assembly to rotate, and a separation member configured to form an axial static seal is disposed between the magnetic power output assembly and the magnetic power input assembly; a front end face of the separation member axially protrudes forward to form a support shaft, the magnetic power output assembly comprises a power output member in connected transmission fit with the cutting tool and a driven magnet fixed to the power output member, the power output member is sleeved over the support shaft, an axial rear end face of the power output member is in rotation fit with an axial front end face of the separation member by using a plane bearing: wherein a decelerator is further disposed between the magnetic power input assembly and the power apparatus, the magnetic power input assembly comprises a power input member sleeved over an output shaft of the decelerator in a circumferential transmission manner and a driving magnet fixed to the power input member, the driving magnet and the driven magnet attract each other in a manner of directly facing each other along the axial direction, an axial gap is disposed between the driving magnet and the separation member and an axial gap is disposed between the driven magnet and the separation member.

2. The magnetic drive medical handpiece according to claim 1, wherein the magnetic power input assembly drives, by using axial magnetic force, the magnetic power output assembly to rotate, the separation member is detachably connected to the handpiece housing, and the magnetic power output assembly rotates and is sleeved over the support shaft in an axial limiting manner.

3. The magnetic drive medical handpiece according to claim 2, further comprising, the plane bearing that limits the magnetic power output assembly backward along the axial direction, the magnetic power output assembly is provided with a shaft hole corresponding to the support shaft, and the plane bearing is located on a front end of the shaft hole.

4. The magnetic drive medical handpiece according to claim 3, wherein a front end outer circle of the support shaft is fixedly provided with a fixed ring, a front end face of the fixed ring supports the plane bearing forward, and an axial rear end face of the fixed ring is used for limiting the magnetic power output assembly forward along the axial direction.

5. The magnetic drive medical handpiece according to claim 4, wherein the plane bearing comprises an annular retainer and a plurality of rollers distributed on the annular retainer along a circumferential direction, and a front end face of the fixed ring is provided with an annular groove configured to guide the plurality of rollers along a circumferential direction.

6. The magnetic drive medical handpiece according to claim 5, wherein a cross section of the annular groove is arc-shaped, the plurality of rollers are balls, and a partial outer wall of each of the balls is embedded into the annular groove in a conformal manner.

7. The magnetic drive medical handpiece according to claim 4, wherein a rear end face of the fixed ring extends backward along the axial direction to form a connection sleeve sleeved over the support shaft, the fixed ring and the connection sleeve form a T-shaped sleeve together, an inner circle of the T-shaped sleeve is fixedly connected to an outer circle of the support shaft.

8. The magnetic drive medical handpiece according to claim 7, wherein the front end outer circle of the support shaft is recessed to form a sinking platform, the inner circle of the T-shaped sleeve is fixedly sleeved over a platform surface of the sinking platform, and the height of the sinking platform is equal to the thickness of the connection sleeve.

9. The magnetic drive medical handpiece according to claim 3, wherein the middle of a front end face of the support shaft protrudes forward along the axial direction to form a mounting column, and the plane bearing is rotatably sleeved over an outer circle of the mounting column.

10. The magnetic drive medical handpiece according to claim 3, wherein a rotation sliding sleeve is disposed in the shaft hole of the magnetic power output assembly, and the rotation sliding sleeve is in rotation fit with the shaft hole.

11. The magnetic drive medical handpiece according to claim 3, wherein the driven magnet is fixed to the rear end face of the power output member, a front end face of the power output member extends forward along the axial direction to form an annular driving claw for driving the cutting tool, a positioning sleeve is fixedly disposed in an inner circle of the annular driving claw, and a rear end face of the positioning sleeve is used for supporting the plane bearing backward.

12. The magnetic drive medical handpiece according to claim 2, wherein the plane bearing comprises an annular retainer and a plurality of balls distributed on the annular retainer along a circumferential direction, the annular retainer is sleeved over the support shaft and is provided with mounting holes for mounting the plurality of balls along the axial direction and a diameter of each of the balls is greater than the axial length of each of the mounting holes.

13. The magnetic drive medical handpiece according to claim 1, wherein the plane bearing comprises an annular retainer and a plurality of balls distributed on the annular retainer along a circumferential direction, the annular retainer is sleeved over the support shaft and is provided with a plurality of mounting holes for mounting the plurality of balls respectively along an axial direction, and a diameter of each of the balls is greater than the axial length of each of the mounting holes.

14. The magnetic drive medical handpiece according to claim 13, wherein an inner circle of the annular retainer extends forward along the axial direction to form a support sleeve, and the support sleeve is radially supported between the power output member and the support shaft in a manner of sliding along a circumferential direction.

15. The magnetic drive medical handpiece according to claim 14, wherein each of the mounting holes is disposed at a joint between the annular retainer and the support sleeve, a diameter of a rear end opening of each of the mounting holes is less than the diameter of each of the balls, a rear end outer circle of the support sleeve is recessed inward along a radial direction to form a semi-arc-shaped groove in communication with a front end opening of each of the mounting holes, each of the balls is embedded into each of the mounting holes by means of engagement between the front end opening of each of the mounting holes and the semi-arc-shaped groove, an arc-shaped annular groove is disposed in the middle of an inner circle of each of the mounting holes, and a radian of the arc-shaped annular groove matches the radian of an outer surface of each of the balls.

16. The magnetic drive medical handpiece according to claim 13, wherein a front end of the support shaft is provided with a limiting ring in a fixed sleeving manner, and an axial rear end face of the limiting ring is used for positioning the power output member along the axial direction; the power output member comprises a power output ring and a driving shift fork formed by means of axial protrusion of a front end face of the power output ring, a plurality of driving shift forks are distributed along a circumferential direction; the magnetic drive medical handpiece further comprises a positioning sleeve for axially positioning the cutting tool, the positioning sleeve is fixedly disposed, in a manner in which an axial rear end face of the positioning sleeve abuts against the power output ring, in an inner circle formed by the plurality of driving shift forks.

17. The magnetic drive medical handpiece according to claim 1, wherein the driving magnet and the driven magnet are both arc-shaped magnetic tiles, a plurality of arc-shaped magnetic tiles are uniformly distributed along a circumferential direction, and same axial ends of two arc-shaped magnetic tiles adjacent in the circumferential direction are heteropoles.

18. The magnetic drive medical handpiece according to claim 1, wherein the separation member is a separation sleeve having a closed front end, an outer circle of the separation sleeve forms an annular step I and is in lap fit with an annular step II disposed in an inner circle of the handpiece housing, to implement axial limitation of the separation sleeve, and an O-shaped seal ring is disposed on an axial opposite surface of the annular step I and the annular step II.

* * * * *